United States Patent [19]

Schwarz

[11] 4,273,566

[45] Jun. 16, 1981

[54] METHOD AND SYSTEM FOR THE FRACTIONATION OF ETHANE-PROPANE MIXTURES

[75] Inventor: Brian L. Schwarz, Pearland, Tex.

[73] Assignee: Cabot Corporation, Kokomo, Ind.

[21] Appl. No.: 44,976

[22] Filed: Jun. 4, 1979

Related U.S. Application Data

[63] Continuation-in-part of Ser. No. 939,460, Sep. 5, 1978, abandoned.

[51] Int. Cl.³ ................................................ F25J 3/02
[52] U.S. Cl. ........................................... 62/27; 62/24
[58] Field of Search ...................................... 62/23–28

[56] References Cited

U.S. PATENT DOCUMENTS

| 2,953,905 | 9/1960 | Chrones et al. | 62/28 |
| 3,398,546 | 8/1968 | Nelson et al. | 62/28 |
| 3,929,438 | 12/1975 | Harper et al. | 62/28 |
| 4,061,481 | 12/1977 | Campbell et al. | 62/28 |

Primary Examiner—Norman Yudkoff
Attorney, Agent, or Firm—B. R. Blaker; J. Schuman; R. F. Dropkin

[57] ABSTRACT

Relatively high pressure mixtures consisting essentially of a major ethane component and a minor, but substantial, propane component are separated into relatively pure ethane and propane fractions by subjecting such mixtures to a number of specific cooling steps and an expansion step preparatory to and in combination with a fractional distillation step. The overhead ethane fraction of the method has a propane content of no greater than about 10 mole percent and is provided in the gas phase. The propane bottom fraction of the method is provided in the liquid phase.

7 Claims, 2 Drawing Figures

METHOD AND SYSTEM FOR THE FRACTIONATION OF ETHANE-PROPANE MIXTURES

CROSS REFERENCE

This application is a continuation-in-part of my prior application, Ser. No. 939,460, filed Sept. 5, 1978, abandoned on an even date herewith.

BACKGROUND OF THE INVENTION

This invention relates to a fractional distillation method and system for the fractionation of the ethane and propane components from relatively high pressure feed streams consisting essentially of a major ethane component and a relatively minor, but substantial, propane component.

In the rectification of wet natural gas, sometimes referred to as "casinghead gas", the condensible hydrocarbons, hereinafter termed "natural gas liquids", are separated, by distillation, from the preponderant methane component. The raw wet gas, in addition to the methane component, commonly comprises variable concentrations of other hydrocarbons such as: ethane, propane, isobutane, n-butane, isopentane, n-pentane, h-hexane and n-heptane. Of these, propane and ethane are usually the predominant non-methane species. Despite the fact that ethane is usually considered to be a non-condensible hydrocarbon species, it nevertheless tends to report in substantial concentration to the natural gas liquids fraction upon distillation of the raw gas.

The natural gas liquids fraction is further refined so as to separate propane and butanes from the pentanes and higher hydrocarbons. The pentanes and higher hydrocarbons comprise a fraction which is generically termed "natural gasoline". The propane and butanes recovered are conventionally marketed as liquified petroleum gas (LPG or LP gases).

The refining of the natural gas liquids fraction by fractionation thereof does not normally result in the recovery of a relatively pure ethane fraction. Rather, the overhead ethane fraction is conventionally recovered as a relatively high pressure mixture consisting essentially of a major ethane component and a relatively minor, but substantial, propane component. Generally, said mixtures consist essentially of between about 70 and about 85 mole percent of the ethane component and between about 30 and about 15 mole percent of the propane component. More typically, the composition of the recovered overhead ethane fraction is within the range of about 75 and about 80 mole percent ethane and between about 25 and about 20 mole percent propane. This recovered overhead ethane-propane fraction arising from the fractionation of natural gas liquids is not susceptible of use as adjunctive fuel in natural gas pipelines since, even under moderate pressures, it normally exists in the liquid state and since, even if first vaporized, it cannot be compressed and introduced into a high pressure natural gas transmission pipeline with immunity from condensation of the propane component thereof.

Were it possible to economically fractionate such ethane-propane mixtures the resulting purified propane fraction would be of greater value as a starting or intermediate material in the petrochemical and synthetic rubber industries. The ethane fraction, on the other hand, if provided in sufficient purity, would constitute a valuable fuel component suitable for introduction as an adjunctive fuel into high pressure natural gas pipeline transmission systems. For such purposes, the ethane fraction is required to have a propane content therein of no greater than about 10 mole percent in order to avoid the condensation problem mentioned above.

Natural gas liquids rectification plants usually produce these relatively impure ethane-propane overhead fractions as a result of consideration of plant economics. In order to accomplish fractionation of the natural gas liquids in a conventional manner such as to result in an ethane overhead fraction of sufficient purity for natural gas pipelining applications there would normally be required substantial additional mechanical refrigeration of the tower condensor in order to condense the relatively pure overhead ethane fraction at a rate sufficient to properly reflux and refrigerate the fractionation tower. To supply such additional mechanical refrigeration would clearly represent relatively enormous costs in terms of the additional equipment required and in terms of the additional operating expenses associated therewith. Too, a relatively pure ethane overhead fraction would strongly tend to exist in the gas phase, thus requiring substantial and relatively expensive compression in order to pipeline this fraction. Moreover, the strong tendency of a relatively pure ethane overhead fraction to exist in the gas phase would also require that both the fractionation tower and the reflux condensor be operated under relatively high pressures in order to maintain the relatively pure ethane condensate in the liquid phase for adequate refluxing of the tower. This too, however, would be detrimental to economic plant operations. As conventionally operated, however, the relatively impure overhead ethane-propane fraction, containing a relatively minor but nevertheless substantial concentration of propane therein, is readily condensed under moderate pressures and without need for substantial mechanical refrigeration of the tower condensor in order to produce the required reflux liquid and refrigerant for the fractionation tower. Additionally, since the conventional relatively impure overhead ethane-propane fraction is readily liquifiable, it can be readily maintained as a liquid at ambient temperatures and transported through pipelines by pumping thereof. Thus, the production of a relatively impure ethane-propane overhead fraction also avoids the necessity for the provision of relatively expensive compressor horsepower which would otherwise attend pipelining of this overhead fraction were it to be produced at substantially higher ethane purity.

In accordance with the present invention there is now provided a method and system by which economic fractionation of such relatively impure ethane-propane mixtures may be had.

OBJECTS OF THE INVENTION

It is a principal object of the present invention to provide a novel method for the fractionation into its components of mixtures consisting essentially of a major ethane component and a relatively minor, but substantial, propane component.

It is another object of the present invention to provide a novel fractionation system for the fractional distillation of mixtures consisting essentially of a major ethane component and a relatively minor, but substantial, propane component.

It is still another object of the invention to provide an improved fractionation method and system for the fractional distillation of mixtures consisting essentially of a major ethane component and a relatively minor, but substantial, propane component wherein the need for ancillary mechanical refrigeration in order to supply adequate refrigeration and reflux liquid to the fractionation tower is avoided.

It is another object of the invention to provide a method for the separation of mixtures consisting essentially of a major ethane component and a relatively minor, but substantial, propane component such as to yield a liquid propane fraction of marketable purity and a gaseous ethane fraction of sufficient purity as to be susceptible of direct use as adjunctive fuel in high pressure natural gas pipeline transmission systems.

SUMMARY OF THE INVENTION

In accordance with the invention, it has been discovered that a relatively high pressure feed mixture consisting essentially of 85 to 70 mole percent ethane and 15 to 30 mole percent propane can be economically fractionally distilled at relatively low pressure to yield an overhead gaseous ethane fraction having a propane content of no greater than about 10 mole percent and a liquid propane bottoms fraction. Instead of carrying out the fractionation of such feed mixtures in a conventional manner whereby the tower overhead is at least partially condensed by a mechanical refrigeration and recycled to the fractionation tower as a refrigerated reflux liquid therefor, the method of the present invention employs for these purposes the feed mixture itself which is pre-cooled, in part, by expansion. In consequence, the method of the invention comprises providing a feed mixture consisting essentially of between 85 and 70 mole percent ethane and between 15 and 30 mole percent propane under relatively high pressure. This feed mixture, if originally provided in an at least partially gaseous state is first fully liquified. The liquid feed mixture is subjected to a number of heat exchange steps whereby it is cooled and whereby the heat extracted therefrom during said steps is employed to heat the cold gaseous overhead ethane fraction from the tower and to provide reboil heat to the fractionation tower. The pressure of the cooled entirely liquid feed mixture is then reduced to a relatively moderate value, by expansion, to further cool the mixture while preserving it in an at least predominantly liquid state. The expanded, cold and predominantly liquid feed mixture is then charged into the top of a fractionation tower wherein it serves as the entire refrigerant and reflux liquid for the tower. The feed mixture is distilled within the tower into (1) a gaseous overhead fraction containing not more than about 10 mole percent propane and (2) a liquid phase bottom propane fraction, said fractions being removed from the tower and collected as products or otherwise suitably employed.

The system of the invention broadly comprises a fractionating tower having a feed inlet, an overhead ethane fraction outlet and a bottoms propane fraction outlet; first and second heat exchangers and expansion cooling means. The cooling legs of said first and second heat exchangers are adapted to receive liquid ethane-propane feed mixture therein under relatively high pressure and to deliver cooled liquid feed mixture therefrom to said expansion cooling means. The warming leg of said first heat exchanger is adapted to receive cold gaseous overhead ethane fraction from the overhead fraction outlet of said tower and to deliver said gaseous fraction as warmed product therefrom. The warming leg of said second heat exchanger is adapted to receive cold liquid from said fractionation tower and to deliver warmed and at least partially vaporized liquid therefrom into said tower for purposes of tower reboil. Said expansion cooling means is adapted to deliver cold predominantly liquid feed mixture therefrom, under moderate pressure, to the feed inlet of the fractionation tower.

THE DRAWING

FIG. 1 hereof is a schematic, diagrammatic flow sheet depicting one embodiment of the system of the invention, wherein the ethane-propane feed mixture is initially provided as a liquid under relatively high pressure.

FIG. 2 hereof is a schematic, diagrammatic flow sheet depicting another embodiment of the invention wherein the ethane-propane feed mixture is initially provided as a gas under high pressure and wherein use is made of a portion of the cold liquid propane bottoms fraction provided by the process to cool and liquify said gaseous feed mixture, to aid reboiling of the tower and to warm the cold propane bottoms fraction thereof.

DESCRIPTION OF PREFERRED EMBODIMENTS

Figure 1:
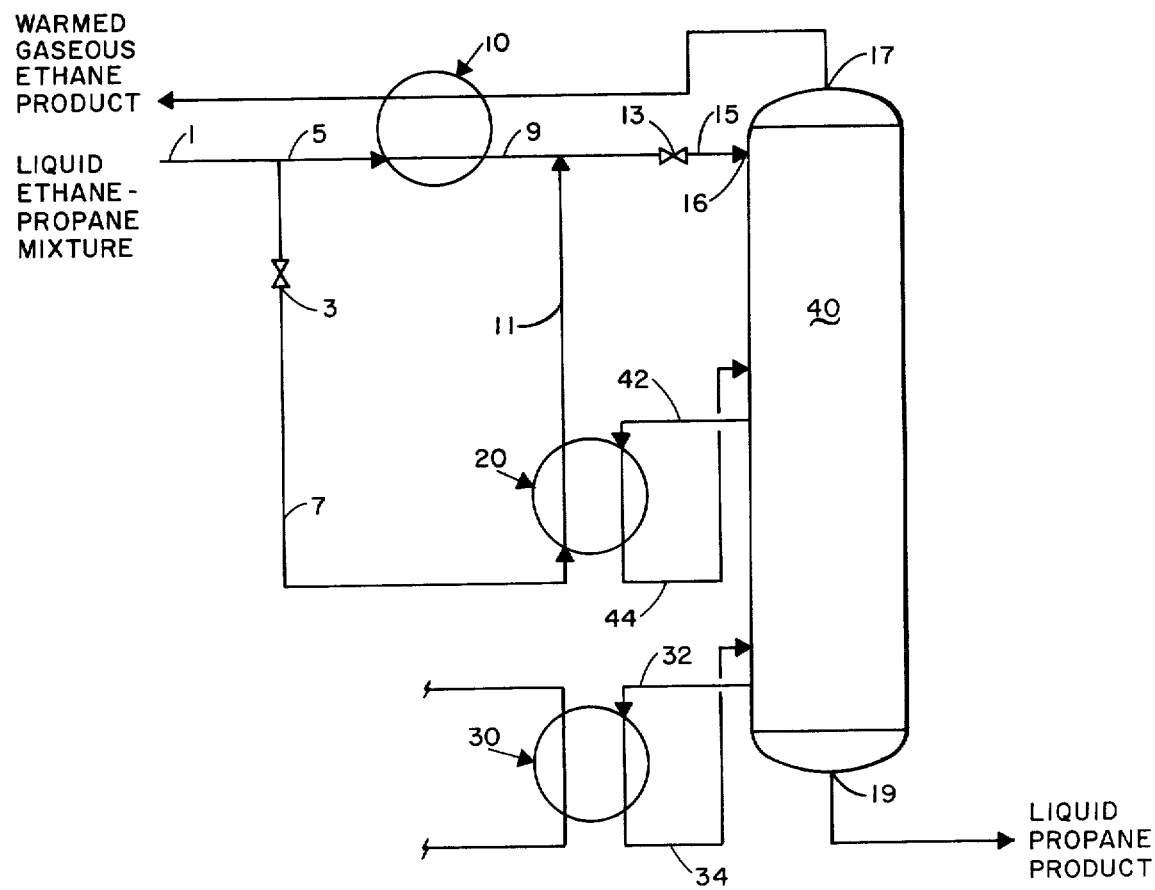
Figure 2:
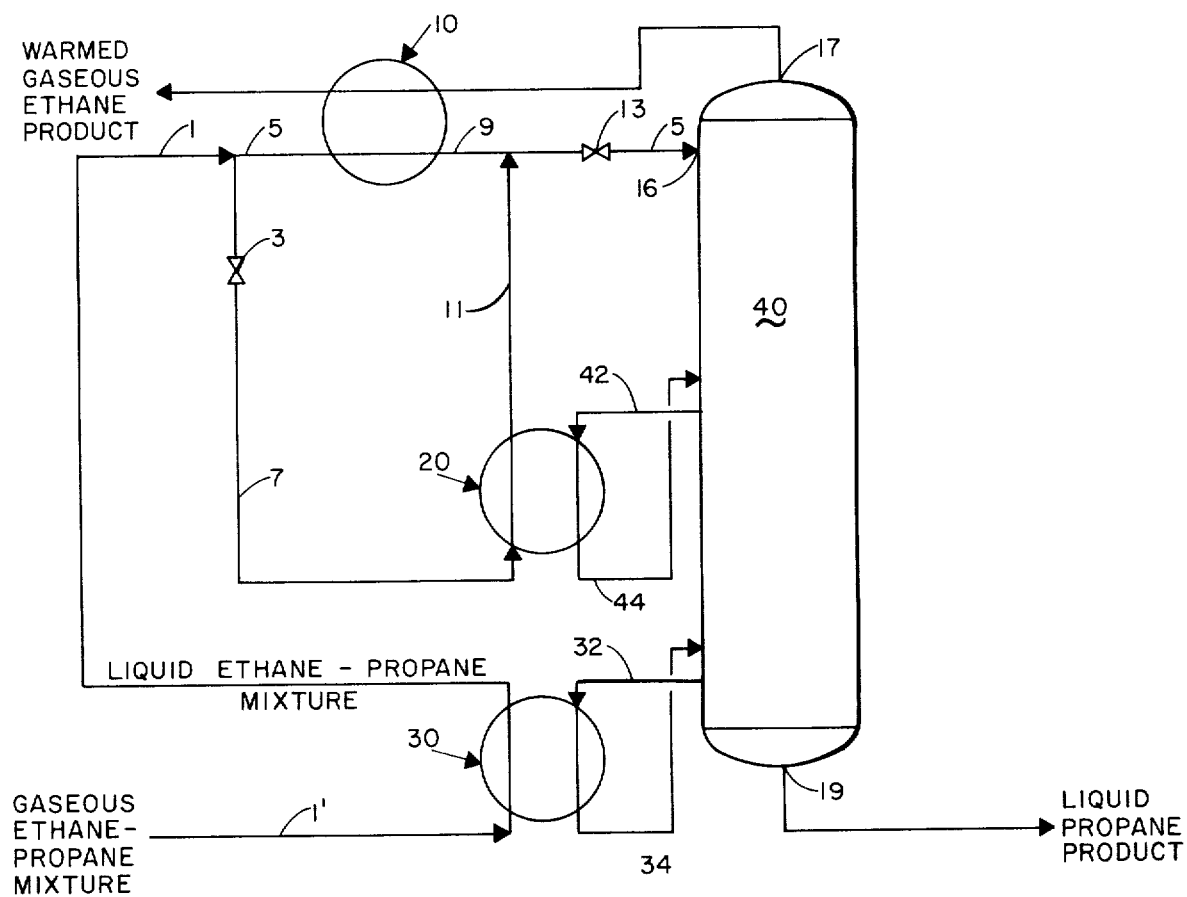

Referring now to FIGS. 1 and 2, wherein like reference numerals refer to like structures, there is provided a completely liquid ethane-propane feed mixture stream 1, under relatively high pressure. While the pressure of said stream 1 is subject to considerable variation, typically it will be on the order of at least about 300 p.s.i.g. and, even more typically, will be at least about 450 p.s.i.g. Liquid feed mixture stream 1 is divided into first and second feed mixture streams 5 and 7, respectively, this division being conveniently achieved by the provision of a valve 3. First feed mixture stream 5 is processed in the cooling leg of a first heat exchanger 10. The warming leg of said heat exchanger 10 receives the cold gaseous overhead ethane fraction from the overhead outlet 17 of fractionation tower 40. By this arrangement, therefore, the first feed mixture stream 5 undergoes a portion of the necessary cooling thereof preliminary to its fractionation while the cold vaporous ethane overhead fraction of fractionation tower 40 is warmed and thermally prepared for use, for instance, as an adjunctive fuel to be injected into a high pressure natural gas pipeline. Second feed mixture stream 7 is received in the cooling leg of second heat exchanger 20. In the case of second heat exchanger 20, however, the warming leg thereof is in recycle communication with fractionation tower 40, thereby to receive through line 42 a portion of the distilling liquid contained in tower 40, to warm and at least partially vaporize it and to return the thusly warmed and at least partially vaporized portion of said liquid into said tower through line 44. Thus, in the arrangement of second heat exchanger 20, not only is the second feed mixture stream 7 cooled but also the distillation occurring in tower 40 is supplied with reboil by the recycle of the warmed and at least partially vaporized tower liquid thereinto. The preliminarily cooled first and second feed mixture streams, streams 9 and 11, respectively, are next subjected to expansion cooling thereof in order to finally prepare them, in terms of both temperature and pressure, for introduction into fractionating tower 40. For purposes of convenience and in order to avoid unnecessary duplication of the expansion cooling equipment, it is generally preferable, although by no means necessary, that the streams 9 and 11 be recombined into a single stream prior to the expansion cooling step. Accordingly, as shown in the drawing, the streams 9 and 11 are first recombined and are then passed as a single stream through an expansion cooling means such as expansion valve 13. Dual functions are served by the expansion cooling step. Firstly, sufficient final precooling of the ethane-propane feed mixture is achieved to prepare said mixture for its refrigerant role in fractionation tower 40. Secondly, the pressure of the feed mixture is reduced from a relatively high pressure to a relatively low pressure whereat said mixture exists in an at least predominantly liquid state. Two criteria should be borne in mind with respect to this cooling step. Firstly, the pressure reduction achieved thereby should be sufficiently great as to cool the mixture to a sufficiently low temperature to operate the tower 40 at the relatively low temperatures required for the desired separation of the ethane and propane components. Secondly, the pressure of the expansion cooled feed mixture stream 15 should be sufficiently high as to assure that the feed mixture exists in an at least predominantly liquid phase, thereby to provide sufficient "reflux" liquid to properly operate the fractionation tower 40. Of course, the expansion cooled feed mixture stream 15 is not, strictly speaking, literally construable as a "reflux" liquid since this latter term is usually taken to involve continuous condensation of the tower overhead and return thereof, as liquid distillates, to the tower. In the present invention, however, this usual reflux condensation of the tower overhead is entirely replaced by the liquid portion of the expansion cooled feed mixture 15 charged into the tower. Accordingly, it is not possible within the context of the present invention to narrowly define specific pressures or pressure drops to be achieved in the expansion cooling step since these will be dictated by many other variables such as the composition of the feed mixture stream 1, the starting pressure and temperature thereof, the particular design and dimensions and reflux liquid requirements of the fractionating tower, and the like. Nevertheless, bearing such considerations in mind, one of ordinary skill can calculate an appropriate reduction in pressure to be achieved in the expansion cooling step of the invention for any particular set of circumstances.

Having thus suitably reduced the temperature and pressure of the ethane-propane feed mixture, said feed mixture, in an at least predominantly liquid state, is introduced as stream 15 into feed inlet 16 of fractionation tower 40. Within tower 40 the ethane component of the mixture is distilled off from the propane component and is exhausted as tower overhead through overhead outlet 17. This cold gaseous ethane overhead fraction is then received into the warming leg of heat exchanger 10 as explained previously. The tower 40 bottoms, comprising the propane fraction of the feed mixture, is removed in the liquid state through bottoms outlet 19. As mentioned, as a result of the cooling and pressure reduction of the feed mixture preparatory to the fractionation thereof in tower 40, said fractionation tower 40 is enabled to be operated under relatively moderate pressures, thereby avoiding the complexities and expenses attendant the design, construction and operations of high pressure vessels.

In order to achieve the intended benefits and operations of the present invention, it is important that feed mixture stream 1 be provided in a completely liquified state and that the composition thereof consist essentially of between 70 and 85 mole percent ethane and between 30 and 15 mole percent propane.

As regards the physical state of feed mixture stream 1, it is necessary that said stream be entirely in the liquid phase in order to assure adequate precooling thereof in first and second heat exchangers 10 and 20 preparatory to the expansion cooling step. Where the feed mixture is initially provided in the gaseous or partially gaseous phase it is, of course, generally possible to completely liquify it by compression, cooling or various combinations of cooling and compression. In order to avoid utilization of additional compression or mechanical refrigeration and in order to avoid even further increases in the already relatively high pressure of the feed mixture provided, it is generally preferred that such preliminary liquifaction, if required, be undertaken solely by cooling of the mixture by extraction of heat therefrom with the tower 40 bottoms. A suitable scheme for liquification of a gaseous feed mixture by cooling with tower bottoms is depicted in FIG. 2 and is described hereinafter in respect of the operations of heat exchanger 30 thereof. Should feed mixture stream 1 be utilized in an at least partially gaseous state, insufficient overall cooling thereof will result, fractionation tower 40 will not be adequately refrigerated solely by means of the feed stream 15 introduced thereinto, and the separation of the ethane and propane fractions within tower 40 will not occur to the extent required to meet the product purity goals of the invention. While it is possible, of course, to employ ancillary mechanical refrigeration of the tower 40 to satisfy such refrigerant deficiencies, such remedial action would be directly contra to yet another goal of the invention, that being to completely avoid the necessity for mechanical refrigeration of the tower or the tower overhead.

The composition of the feed mixture is also of substantial importance in providing the salubrious environment necessary to the successful undertaking of the invention. Accordingly, by the term "consisting essentially of", it is intended that the feed mixtures employed for purposes of the invention contain no more than about 5 mole percent, in the aggregate, of any one or more hydrocarbon species higher than propane, and, additionally, that said mixture contain no more than about 3 mole percent of methane. Where the methane content of the feed mixture is substantially greater than about 3 mole percent, for instance 5 mole percent, substantial difficulties can attend the liquifaction of an at least partially gaseous feed mixture and/or the maintenance of the feed mixture in the liquid state throughout the heat exchange steps undertaken in heat exchangers 10 and 20. Such difficulties would tend to be resoluble only by use of mechanical refrigeration of the mixture in addition to the refrigeration thereof provided by the ethane overhead fraction and tower liquids.

Under those circumstances wherein the proposed feed mixture contains more than about 5 mole percent, in the aggregate, of hydrocarbon species higher than propane, the presence of such higher hydrocarbon(s) would require excessive additional reboil heat to be supplied to tower 40 in order to effectively reboil the tower. Naturally, the higher the heat load applied to the tower by reason of increased reboil requirements, the greater will be the offsetting refrigerant requirements therefor to maintain the tower at a sufficiently low temperature to achieve the desired ethane/propane separation. In the present invention, the entirety of the refrigerant requirements of the tower is supplied by the expansion cooled, predominantly liquid feed mixture introduced thereinto under moderate pressure. This highly desirable and necessary feature of the invention becomes excessively difficult to obtain where the reboil requirements of the tower are increased due to the presence of greater than about 5 mole percent, in the aggregate, of $C_4$ and higher hydrocarbon(s) in the feed mixture.

In order to control the concentration of ethane in the liquid propane fraction removed from the tower bottom, a third heat exchanger 30, the warming leg of which is in recycle communication with the lower portion of fractionation tower 40, is provided as a tower reboiler. Thus, a portion of the liquid propane fraction is taken as stream 32 from the lower portion of tower 40, warmed and at least partially vaporized in exchanger 30, and returned to the tower 40 as stream 34. Substantially any suitable heat supplying fluid can be employed in the warming leg of heat exchanger 30. In FIG. 1, for example, said heat supplying fluid can comprise heater water or steam derived from a fired heater (not shown). As shown in FIG. 2, a high pressure gaseous feed mixture stream 1' can also often be beneficially employed as the heat supplying fluid to heat exchanger 30. Accordingly, in the flow diagram of FIG. 2, the high pressure feed stream is cooled in three incremental stages. The first of these is that which occurs in exchanger 30 wherein the gaseous feed mixture is cooled to liquifaction and reboil is provided to the tower 40 bottoms. The second cooling stage occurs in the combination of exchangers 10 and 20. The third cooling stage is defined as the expansion cooling step. In the flow diagram of FIG. 1, the high pressure liquid feed mixture initially provided is subjected to two precooling stages, the first being that accomplished in heat exchangers 10 and 20 and the second stage being that achieved in the expansion cooling step at 13.

I am aware of no unusual criticalities attending the design, materials and construction of the heat exchangers 10, 20 or 30 or the fractionation tower 40. Such equipments are well known in the natural gas liquids refining arts and, therefore, require no extensive discussion herein. The fractionation tower 40, for instance, can be of the bubble-cap plate, sieve plate or packed type. Similarly, the heat exchangers 10, 20 and 30 can each of any suitable bi-fluid design such as shell and tube, spiral tube, double pipe or bayonet tube.

As an example of the operations of a system such as disclosed in FIG. 1, the following is representative of one set of typical calculated temperatures and pressures of several of the streams coursing through the system:

Initial Feed Mixture, Stream 1: liquid phase composition consisting essentially of 80 mole percent ethane and 20 mole percent propane, supplied at a temperature of 80° F. and at an inlet pressure of 480 p.s.i.g.
Stream 11: 20° F., liquid phase.
Stream 9: 20° F., liquid phase.
Stream 15: 100 p.s.i.g., −30° F., predominantly liquid phase.
Overhead ethane stream at outlet 17: −26° F., gas phase, (≦10 mole percent propane).
Overhead ethane stream after warming in heat exchanger 10: 60° F., gas phase.
Fractionation tower 40: 100 p.s.i.g.
Propane bottoms stream at bottoms outlet 19: 100 p.s.i.g., 64° F., liquid phase.

Similarly, as an example of the operations of a system such as disclosed in FIG. 2, the following is representative of another set of typical calculated temperatures and pressures of several of the streams coursing through the system:

Initial Feed Mixture, Stream 1': gas phase composition consisting essentially of 80 mole percent ethane and 20 mole percent propane, supplied at a temperture of 100° F. and at an inlet pressure of 480 p.s.i.g.
Stream 1: 80° F., liquid phase.
Stream 11: 20° F., liquid phase.
Stream 9: 20° F., liquid phase.
Stream 15: 100 p.s.i.g., −30° F., predominantly liquid phase
Overhead ethane stream at outlet 17: −26° F., gas phase, (≦10 mole percent propane).
Overhead ethane stream after warming in heat exchanger 10: 60° F., gas phase.
Fractionating tower 40: 100 p.s.i.g.
Propane bottoms stream at bottoms outlet 19: 100 p.s.i.g., 68° F., liquid phase.

Accordingly, while the invention has been described herein with reference to certain preferred embodiments thereof, it will be understood by those skilled in the art that various changes in equivalents may be made to adapt the invention to particular situations. Therefore, although specific preferred embodiments of the present invention have been described in detail above, the description is not intended to limit the invention to these embodiments alone since they are intended to be recognized as illustrative rather than as restrictive or limiting of the invention. Thus, the invention is not to be construed as being limited to the details disclosed herein but may be modified within the scope of the appended claims.

What is claimed is:

1. A method for the fractionation of ethane-propane mixtures which comprises the steps of:
   (a) providing a relatively high pressure entirely liquid feed mixture consisting essentially of between 85 and 70 mole percent ethane and between 15 and 30 mole percent propane:
   (b) dividing said liquid feed mixture into first and second feed mixture streams;
   (c) cooling and reducing the pressure of said liquid feed mixture to a temperature sufficiently low to supply all of the refrigeration in the fractionation step of (d), below, and to a relatively low pressure whereat said mixture is maintained in an at least predominantly liquid state, thereby to provide all of the liquid for refluxing purpose in said fractionation step of (d), said first stream being precooled by heat exchange thereof with cold gaseous ethane fraction removed as overhead product from the fractionation tower of step (d), said second stream being precooled by heat exchange thereof with cold distilling liquid removed from the fractionation tower of step (d), said distilling liquid being recycled to the fractionation tower after warming and at least partial vaporization thereof by said second stream to thereby provide reboil heat to said tower, said cooling and pressure reduction being at least partially achieved by expansion cooling of said liquid feed mixture substantially immediately preceding said step (d);
   (d) introducing the cooled pressure-reduced and at least predominantly liquid feed mixture of (c) into a fractionation tower wherein fractionation of the ethane component from said mixture is achieved at relatively low pressure;

(e) removing as overhead product from said fractionation tower, and without reflux condensation thereof, a cold gaseous ethane fraction having a propane content of no greater than about 10 mole percent; and (f) removing as bottom product from said fractionation tower a liquid propane fraction having reduced ethane content.

2. The method of claim 1 wherein said relatively high pressure feed mixture of (a) has a pressure of at least 450 p.s.i.g.

3. The method of claim 1 wherein said feed mixture consists essentially of between 80 and 75 mole percent ethane and between 20 and 25 mole percent propane.

4. The method of claim 1 wherein the precooled first and second feed mixture streams are recombined into a single stream prior to expansion cooling thereof.

5. The method of claim 1 wherein a portion of the liquid propane fraction contained in the bottom of the fractionation tower is removed therefrom, warmed and at least partially vaporized by heat exchange with a fluid and recycled into the bottom portion of the tower, thereby to provide reboil heat to the tower.

6. The method of claim 5 wherein said fluid is an at least partially gaseous relatively high pressure feed mixture stream whereby said stream is cooled to entire liquifaction thereof while said portion of said liquid propane fraction is warmed.

7. The method of claim 1 wherein said gaseous overhead ethane fraction is introduced into a natural gas pipeline transmission system as an adjunctive fuel therefor.

* * * * *